US00PP17570P2

(12) United States Plant Patent
Smith

(10) Patent No.: US PP17,570 P2
(45) Date of Patent: Apr. 3, 2007

(54) ***HIBISCUS* PLANT NAMED 'SPLASH YOPINOT GRIGIO'**

(50) Latin Name: *Hibiscus moscheutos*
Varietal Denomination: Splash Yopinot Grigio

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 50 days.

(21) Appl. No.: 11/177,995

(22) Filed: Jul. 8, 2005

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct *Hibiscus* plant named 'Splash Yopinot Grigio', characterized by its upright and outwardly spreading plant habit; freely branching and moderately vigorous growth habit; early flowering habit; large white single flowers with red purple-colored centers and blushed with red purple towards the margins; and excellent garden performance.

2 Drawing Sheets

Botanical designation: *Hibiscus moscheutos.*
Cultivar denomination: 'Splash Yopinot Grigio'.

BACKGROUND OF THE INVENTION

The present invention relates to a new and distinct cultivar of *Hibiscus,* botanically known as *Hibiscus moscheutos,* and hereinafter referred to by the name 'Splash Yopinot Grigio'.

The new *Hibiscus* is a product of a planned breeding program conducted by the Inventor in Alva, Fla. The objective of the breeding program is to create new freely-branching and *Hibiscus* cultivars with a compact plant habit and attractive flower coloration.

The new *Hibiscus* originated from a cross-pollination made by the Inventor in Alva, Fla. during the summer of 2001, of the *Hibiscus moscheutos* cultivar Disco Belle Pink, not patented, as the female, or seed, parent with the *Hibiscus moscheutos* cultivar Blue River II, not patented, as the male, or pollen, parent. The cultivar Splash Yopinot Grigio was discovered and selected by the Inventor as a flowering plant within the progeny of the stated cross-pollination in a controlled environment in Alva, Fla. in May, 2002.

Asexual reproduction of the new *Hibiscus* by vegetative terminal cuttings in a controlled environment in Alva, Fla. since June, 2002, has shown that the unique features of this new *Hibiscus* are stable and reproduced true to type in successive generations.

SUMMARY OF THE INVENTION

The cultivar Splash Yopinot Grigio has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Splash Yopinot Grigio'. These characteristics in combination distinguish 'Splash Yopinot Grigio' as a new and distinct cultivar:

1. Upright and outwardly spreading plant habit.
2. Freely branching and moderately vigorous growth habit.
3. Early flowering habit.
4. Large white-colored single flowers blushed with red purple-colored centers and blushed with red purple towards the margins.
5. Excellent garden performance.

Plants of the new *Hibiscus* can be compared to plants of the female parent, the cultivar Disco Belle Pink. Plants of the new *Hibiscus* differ from plants of the cultivar Disco Belle Pink in the following characteristics:

1. Plants of the new *Hibiscus* are fuller than plants of the cultivar Disco Belle Pink.
2. Plants of the new *Hibiscus* flower about two days later than plants of the cultivar Disco Belle Pink.
3. Plants of the new *Hibiscus* have larger flowers than plants of the cultivar Disco Belle Pink.
4. Plants of the new *Hibiscus* and the cultivar Disco Belle Pink differ in flower coloration as plants of the cultivar Disco Belle Pink have more intense red purple-colored blushing towards the margins.

Plants of the new *Hibiscus* can be compared to plants of the male parent, the cultivar Blue River II. Plants of the new *Hibiscus* differ from plants of the cultivar Blue River II in the following characteristics:

1. Plants of the new *Hibiscus* are shorter and fuller than plants of the cultivar Blue River II.
2. Plants of the new *Hibiscus* have lighter green-colored foliage than plants of the cultivar Blue River II.
3. Plants of the new *Hibiscus* flower about two days earlier than plants of the cultivar Blue River II.
4. Plants of the new *Hibiscus* and the cultivar Blue River II differ in flower coloration as plants of the cultivar Blue River II have white-colored flowers.

Plants of the new *Hibiscus* can be compared to plants of the *Hibiscus* cultivar Disco Belle White, not patented. In side-by-side comparisons conducted in Alva, Fla., plants of the new *Hibiscus* differed from plants of the cultivar Disco Belle White in the following characteristics:

1. Plants of the new *Hibiscus* were shorter and fuller than plants of the cultivar Disco Belle White.
2. Plants of the new *Hibiscus* flowered about three days later than plants of the cultivar Disco Belle White.
3. Plants of the new *Hibiscus* had larger flowers than plants of the cultivar Disco Belle White.
4. Plants of the new *Hibiscus* and the cultivar Disco Belle White differed in flower color as plants of the cultivar Disco Belle White did not have red purple-colored blushing towards the margins.

Plants of the new *Hibiscus* can also be compared to plants of the *Hibiscus* cultivar Luna Blush, not patented. In side-by-side comparisons conducted in Alva, Fla., plants of the new *Hibiscus* differed from plants of the cultivar Luna Blush in the following characteristics:

1. Plants of the new *Hibiscus* were taller than plants of the cultivar Luna Blush.
2. Plants of the new *Hibiscus* flowered about three days later than plants of the cultivar Luna Blush.
3. Plants of the new *Hibiscus* had larger flowers than plants of the cultivar Luna Blush.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph on the first sheet comprises a side perspective view of a typical flowering plant of 'Splash Yopinot Grigio' grown in an outdoor nursery in Alva, Fla. for about six months.

The photograph on the second sheet comprises a close-up view of a typical flower of 'Splash Yopinot Grigio'.

DETAILED BOTANICAL DESCRIPTION

The following observations, measurements and values describe plants grown in Alva, Fla. in one-gallon containers in a polypropylene-covered shadehouse during the summer and under conditions which closely approximate commercial production. During the production of the plants, day temperatures ranged from 29° C. to 32° C. and night temperatures ranged from 21° C. to 24° C. Plants were pinched about one month after planting. The description was taken about two months after the pinch. In the description, color references are made to The Royal Horticultural Society Colour Chart, 1995 Edition, except where general terms of ordinary dictionary significance are used.

Botanical classification: *Hibiscus moscheutos* cultivar Splash Yopinot Grigio.

Parentage:

*Female or seed parent.*—*Hibiscus moscheutos* cultivar Disco Belle Pink, not patented.

*Male or pollen parent.*—*Hibiscus moscheutos* cultivar Blue River II, not patented.

Propagation:

*Type.*—By vegetative terminal cuttings.

*Time to initiate roots, summer.*—About eight days at temperatures of 30° C.

*Time to initiate roots, winter.*—About ten days at temperatures of 21° C.

*Time to develop roots, summer.*—About 12 to 14 days at temperatures of 30° C.

*Time to develop roots, winter.*—About 18 to 21 days at temperatures of 21° C.

*Root description.*—Thick, fibrous; white in color.

*Rooting habit.*—Freely branching.

Plant description:

*Plant form and growth habit.*—Perennial shrub; upright and outwardly spreading plant habit. Moderately vigorous growth habit.

*Branching habit.*—Freely branching, lateral branches potentially forming at every node.

*Plant height.*—About 37.5 cm.

*Plant diameter* (*area of spread*).—About 45 cm.

*Lateral branch description.*—Length: About 28 cm. Diameter: About 7.5 mm. Internode length: About 2.1 cm. Texture: Smooth, glabrous. Color: 146A.

*Foliage description.*—Arrangement: Alternate, simple. Length: About 9.6 cm. Width: About 7.1 cm. Shape: Cordate to ovate. Apex: Acute; narrowly tapering. Base: Cordate. Margin: Crenate; slightly undulate. Texture, upper and lower surfaces: Smooth, glabrous. Venation pattern: Palmate. Color: Developing foliage, upper surface: Darker green than 147A. Developing foliage, lower surface: Close to 191A. Fully expanded foliage, upper surface: Close to 147A. Fully expanded foliage, lower surface: Close to 147B. Venation, upper surface: Close to 146A. Venation, lower surface: 146B. Petiole: Length: About 3.4 cm. Diameter: About 3.5 mm. Texture, upper and lower surfaces: Smooth, glabrous. Color, upper surface: Close to 146B. Color, lower surface: Close to 146A.

Flower description:

*Flower arrangement.*—Flowers develop at axillary leaf axils; typically one or two flowers per axil. Flowers face upright to outward.

*Flower appearance.*—Rotate white-colored flowers with red purple-colored centers and blushed with red purple towards the margins. Flowers are open for about two days. Flowers persistent.

*Natural flowering season.*—Usually spring and summer or during periods of warm weather.

*Flower diameter.*—About 12 cm.

*Flower length* (*height*).—About 2.8 cm.

*Flower bud.*—Length: About 1.7 cm. Diameter: About 1.3 cm. Shape: Ovoid. Color: Close to 147B.

*Petals.*—Quantity/arrangement: Corolla consists of five petals; petals imbricate. Length: About 6 cm. Width: About 6.2 cm. Shape: Roughly orbicular. Apex: Rounded; undulate. Base: Attenuate. Margin: Entire to slightly crenate; undulate. Texture, upper and lower surfaces: Smooth, glabrous; satiny; rugose. Color: When opening and fully opened, upper surface: Close to 155D; towards the base, 66A; slightly overlain with 66A towards the margins. When opening and fully opened, lower surface: Close to 155D.

*Sepals.*—Quantity/arrangement: Five sepals fused into a tubular calyx. Length: About 1.4 cm. Width: About 1 cm. Shape: Oblong. Apex: Cuspidate. Margin: Entire. Texture, upper surface: Smooth, glabrous. Texture, lower surface: Slightly pubescent. Color, upper surface: 146A to 146B. Color, lower surface: 146A.

*Bracts.*—Quantity/arrangement: About twelve in a single whorl. Length: About 1.3 cm. Width: About 3 mm. Shape: Lanceolate. Apex: Sharply acute. Margin: Entire. Texture, upper and lower surfaces: Slightly pubescent. Color, upper surface: Close to 146A. Color, lower surface: Between 146A and 147A.

*Peduncles.*—Length: About 2.9 cm. Diameter: About 2 mm. Angle: Straight to slightly bent. Strength: Strong, flexible. Texture: Smooth, glabrous. Color: Close to 146A.

*Reproductive organs.*—Androecium: Stamen quantity per flower: Numerous, about 100. Anther shape: Reniform. Anther size: About 2 mm by 1 mm. Anther color: Close to 4D. Amount of pollen: None observed. Gynoecium: Pistil quantity per flower: One with five stigmas. Pistil length: About 3.1 cm. Style length: About 2.1 cm. Style color: Close to 155D. Stigma shape: Rounded. Stigma color: Close to 154C to 154D. Ovary color: Close to 144A.

*Seed/fruit.*—Seed and fruit production has not been observed.

Garden performance: Plants of the new *Hibiscus* have been observed to be tolerant to wind and rain and to have excellent garden performance.

Hardiness: Plants of the new *Hibiscus* have been observed to be hardy to USDA Zone 5.

High temperature tolerance: Plants of the new *Hibiscus* have been observed to tolerate temperatures of about 40° C.

Disease/pest resistance: Plants of the new *Hibiscus* have not been observed to be resistant to pathogens and pests common to *Hibiscus*.

It is claimed:

1. A new and distinct *Hibiscus* plant named 'Splash Yopinot Grigio', as illustrated and described.

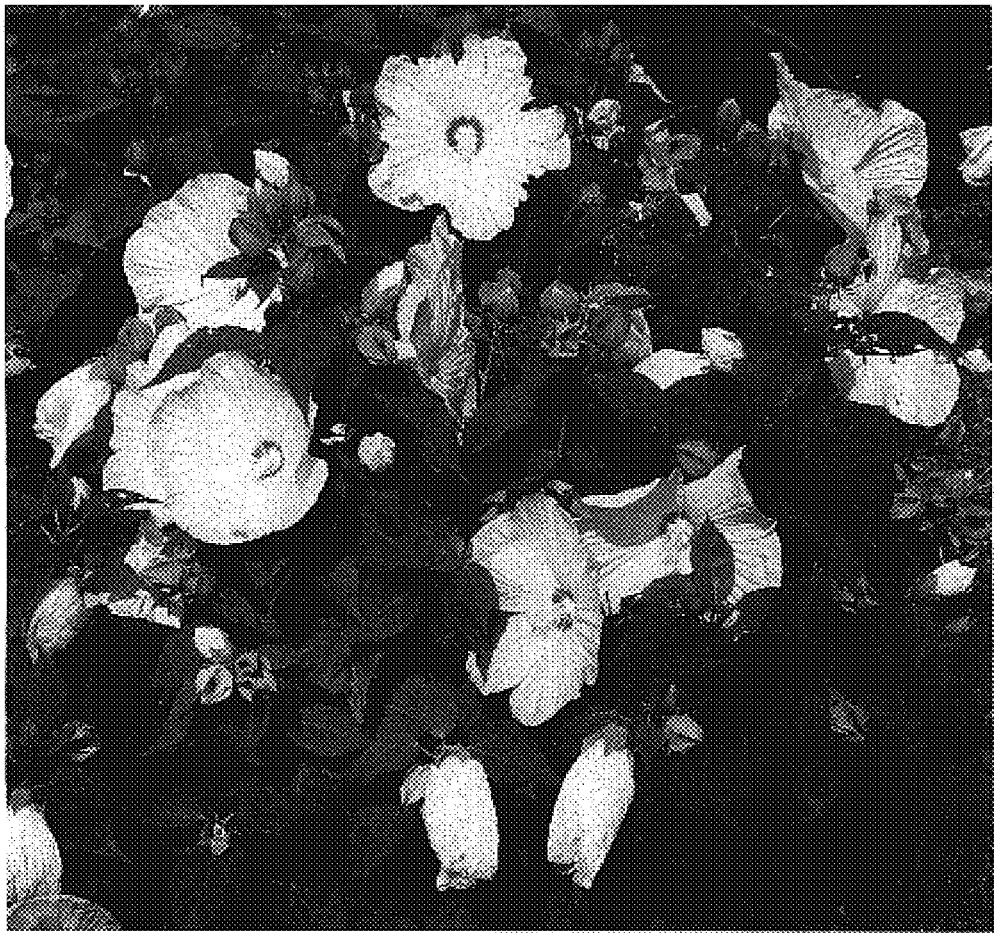

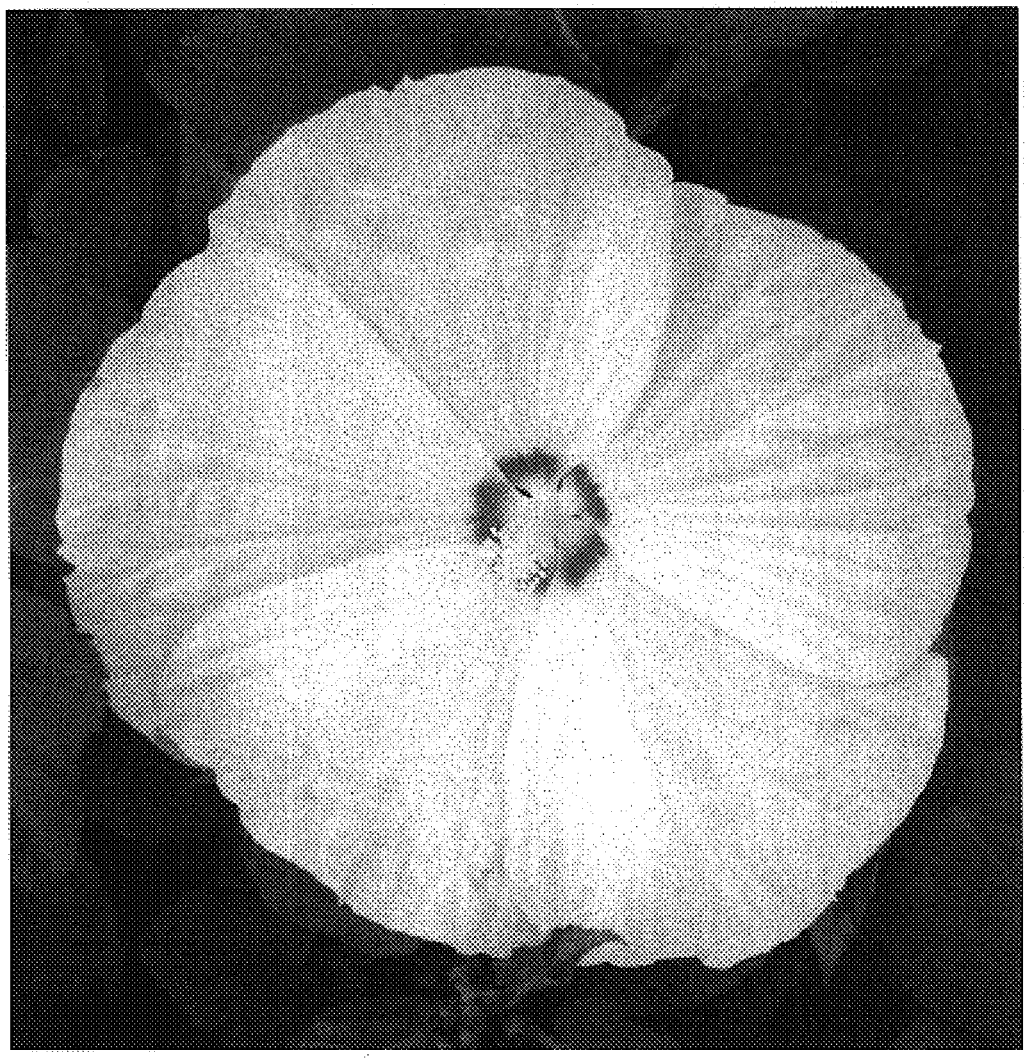

* * * * *